United States Patent [19]

Harnisch

[11] 4,016,172
[45] Apr. 5, 1977

[54] AZOLINDOLINES AND AZOLINDOLINE DYESTUFFS

[75] Inventor: Horst Harnisch, Cologne, Germany

[73] Assignee: Bayer Aktiengesellschaft, Leverkusen, Germany

[22] Filed: Jan. 17, 1974

[21] Appl. No.: 434,022

Related U.S. Application Data

[62] Division of Ser. No. 179,181, Sept. 9, 1971, Pat. No. 3,840,552.

[30] Foreign Application Priority Data

Sept. 9, 1970 Germany .......................... 2044620

[52] U.S. Cl. ...................... 260/307 D; 260/240 G; 260/304 R; 260/309.2
[51] Int. Cl.² ....................................... C07D 263/56
[58] Field of Search ........ 260/307 D, 309.2, 304 R, 260/240 G

[56] References Cited

UNITED STATES PATENTS

| | | | |
|---|---|---|---|
| 2,425,774 | 8/1947 | Wilson | 260/298 |
| 3,468,619 | 9/1969 | Rave et al. | 8/25 |
| 3,723,419 | 3/1973 | Mee et al. | 260/240.6 |
| 3,840,552 | 10/1974 | Harnisch | 260/307 D |

OTHER PUBLICATIONS

Theilheimer—"Synthetic Methods of Organic Chemistry"—vol. 22 (1968), — S. Karger, publ. — pp. 353–354.

*Primary Examiner*—Raymond V. Rush
*Attorney, Agent, or Firm*—Plumley and Tyner

[57] ABSTRACT

Azolindolines of the formula

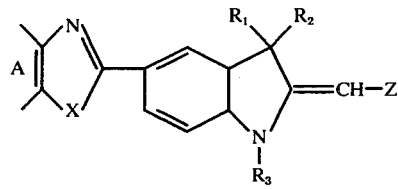

wherein
  Z represents hydrogen or an optionally modified aldehyde group,
  $R_1$ and $R_2$ denote alkyl or represent the remaining members of a cycloalkyl radical,
  $R_3$ denotes alkyl or aralkyl,
  X represents oxygen, sulphur or $-NR_4$,
wherein
  $R_4$ denotes hydrogen or alkyl, cycloalkyl or aralkyl, and A represents the remaining members of an aromatic radical, as well as their preparation, and, moreover, compounds of the formula

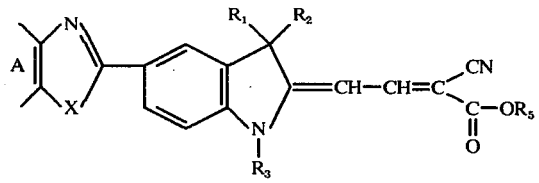

wherein
  A, X, $R_1$, $R_2$ and $R_3$ have the same meaning as above and $R_5$ denotes alkyl or aralkyl as well as their preparation and their use for the dyeing of synthetic fiber materials.

6 Claims, No Drawings

AZOLINDOLINES AND AZOLINDOLINE DYESTUFFS

This is a division of application Ser. No. 179,181 filed 9/9/71, now U.S. Pat. No. 3,840,552.

The subject of the present invention are azolindolines of the general formula

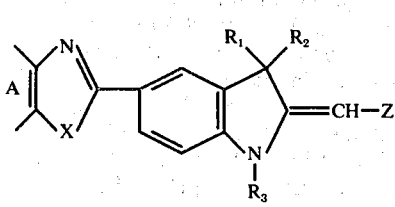

wherein
- Z represents hydrogen or an optionally modified aldehyde group,
- $R_1$ and $R_2$ denote alkyl radicals or represent the remaining members of a cycloalkyl radical,
- $R_3$ denotes an alkyl or aralkyl radical, X represents oxygen, sulphur or $=NR_4$, wherein
- $R_4$ denotes hydrogen or an alkyl, cycloalkyl or aralkyl radical, and
- A represents the remaining member of an aromatic radical, as well as processes for their manufacture.

By modified aldehyde groups there are especially to be understood acetals, hydrates, ammoniates, aminals, bisulphite adducts, azomethines and hydrazones.

Possible aromatic radicals of which the remaining members are designated A, are both radicals of monocyclic ring systems and radicals of bicyclic ring systems, which can be built up of aromatic-carbocyclic and/or aromatic-heterocyclic rings in any desired fusion arrangement, and which can optionally also contain fused-on partially saturated, five-membered or six-member rings.

As examples of such aromatic radicals there may, for example, be mentioned: the radicals of benzene, naphthalene, tetralin, indane, acenaphthene, pyridine, quinoline, pyrimidine, quinoxaline and indazole. Carbocyclinc radicals are preferred.

These aromatic radicals can also possess substituents, such as halogen, cycloalkyl, aralkyl, phenyl, alkyl, alkoxy, alkysulphonly, aralkylsulphonyl, dialkylaminosulphonyl, alkoxycarbonyl, dialkylaminocarbonyl and acylamino radicals.

By the abovementioned alkyl radicals there are preferably to be understood those with 1 to 5 C atoms, which can possess further substituents, such as halogen, hydroxyl and alkoxy. Suitable alkyl radicals of this nature are, for example, methyl, trifluoromethyl, ethyl, chloroethyl, bromoethyl, hydroxyethyl, methoxyethyl, n-propyl, isopropyl and n-, i- and t-butyl.

Suitable aralkyl radicals are especially the benzyl radical and the phenylethyl radical.

A suitable cycloalkyl radical is, for example, the cyclohexyl radical. Suitable alkoxy radicals are above all those with 1 to 5 C atoms. As alkylsulphonyl radicals, the methtlsulphonyl and ethylsulphonyl radical should especially be mentioned, and as aralkylsulphonyl radicals the benzylsulphonly radical should especially be mentioned. Suitable dialkylaminosulphonyl and dialkylaminocarbonyl radicals are preferably those which contain methyl and ethyl groups.

As alkoxycarbonyl radicals, the methoxycarbonyl, ethoxycarbonyl and β-methoxy-ethoxycarbonyl radicals should for example be mentioned.

Suitable acylamino radicals are, for example, acetylamino, propionylamino and methylsulphonylamino radicals.

Preferred alkyl radicals $R_1$ and $R_2$ are methyl and ethyl radicals. Suitable cycloalkyl radicals which can be formed by $R_1$ and $R_2$ together are cyclohexyl and cyclopentyl radicals.

Suitable alkyl radicals $R_3$ and $R_4$ are, for example, alkyl or alkenyl radicals with 1 to 5 atoms, which can also possess further substituents, such as halogen, hydroxyl, alkoxy, nitrile, alkylcarbonyl, benzoyl and alkoxycarbonyl radicals. Suitable alkyl radicals, of this nature are, for example, methyl, ethyl, chloroethyl, bromoethyl, fluoroethyl, cyanoethyl, methoxyethyl, allyl, n-propyl, isopropyl, δ-hydroxybutyl, acetonyl, phenacyl, methoxycarbonylethyl and n-butyl. Methyl and ethyl radicals are preferred.

The new azolindolines of the formula (I) are accessible according to various processes. One of these processes is characterised in that azolindolenines of the formula

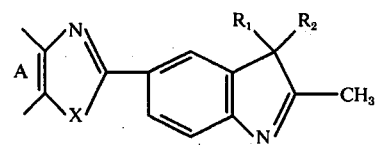

wherein

A, X, $R_1$ and $R_2$ have the abovementioned meaning, are first reacted with alkylating agents or aralkylating agents to give compounds of the formula

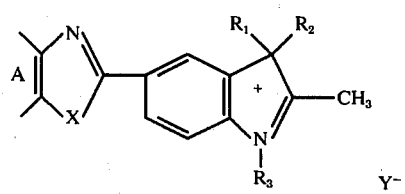

wherein
- A, X, $R_1$, $R_2$ and $R_3$ have the abovementioned meaning and
- Y represents the anionic radical originating from the alkylating or aralkylating agent, these are converted in a manner which is in itself known, under alkaline conditions, into the azolindolines of the formula

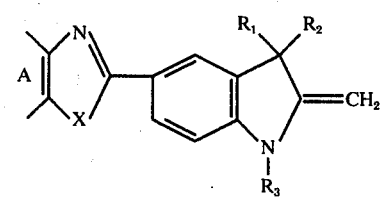

wherein
- A, X, $R_1$, $R_2$ and $R_3$ have the abovementioned meaning, and these are, if desired, reacted according to formylation methods which are in themselves known to give aldehydes of the formula

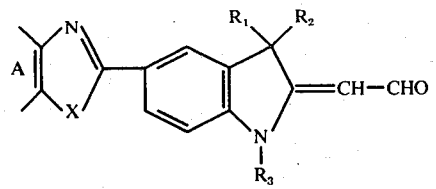

wherein

A, X, $R_1$, $R_2$ and $R_3$ have the mentioned meaning.

It must be desired as distinctly surprising that the reaction, according to the invention, of (II) with alkylating agents to give (III) takes place selectively at the indolenine nitrogen and that practically no quaternisation of the azole nitrogen occurs. This unforeseeable effect is of decisive importance because with quaternary azoles there is the danger, especially under alkaline conditions, of hydrolytic ring opening.

In carrying out the quaternisation, an appropriate procedure is to react approximately equimolar amounts of the reactants in a solvent which is inert under the reaction conditions, such as benzene, toluene, chlorobenzene, o-dichlorobenzene, chloroform, carbon tetrachloride, dioxane, ethyl acetate or acetonitrile, with one another at temperatures between 25° and 130° C.

Suitable azolindolenines of the formula (II) are, for example: 2,3,3-trimethyl-5-[5'-methyl-benzoxazolyl-(2')]-indolenine, 2,3,3-trimethyl-5-[5'-chloro-benzoxazolyl-(2')]-indolenine, 2-methyl-3,3-diethyl-5-[5'-trifluoromethyl-benzoxazolyl-(2')]-indolenine, 2,3-dimethyl-3-ethyl-5-]5'-cyclohexyl-benzoxazolyl-(2')]-indolenine, 2,3,3-trimethyl-5-[5'-phenyl-benzoxazolyl-(2')]-indolenine, 2,3,3-trimethyl-5-[5'-methoxy-benzoxazolyl-(2')]-indolenine, 2,3,3-trimethyl-5-[5',6'-dimethyl-benzoxazolyl-(2')]-indolenine, 2,3,3-trimethyl-5-[5'-bromo-benzoxazolyl-(2')]-indolenine, 2,3,3-trimethyl-5-[5'-tertiary-butyl-benzoxazolyl-(2')]-indolenine, 2,3,3-trimethyl-5-[5'-fluoro-benzoxazolyl-(2')]-indolenine, 2,3,3-trimethyl-5-[5'-ethyl-benzoxazolyl-(2')]indolenine, 2,3,3-trimethyl-5-[5'-ethylsulphonyl-benzoxazolyl-(2')]-indolenine, 2,3,3-trimethyl-5-[5'-dimethylaminosulphonyl-benzoxazolyl-(2')]-indolenine, 2,3,3-trimethyl-5-[5'-β-bromoethyl-benzoxazolyl-(2')]-indolenine, 2,3,3-trimethyl-5-]5'-acetylamino-benzoxazolyl-(2'2')]-indolenine, 2,3,3trimethyl-5-[5'-β-hydroxyethyl-benzoxazolyl-(2')]-indolenine, 2,3,3-trimethyl-5[5'-benzyl-benzoxazolyl-(2')]-indolenine, 2-methyl-3,3-pentamethylene-5-benzoxazolyl- (2')-indolenine, 2,3,3-trimethyl-5[5'-β-phenylethyl-benzoxazolyl-(2')]-indoklenine, 2,3,3-trimethyl-5-[5'-β-chloroethyl-benzoxazlyl-(2')]-indolenine, 2,3,3-trimethyl-5-[5'-methylsulphonyl-benzoxazolyl-(2')]-indolenine, 2,3,3-trimethyl-5-[-5'-diethylaminosulphonyl-benzoxazolyl-(2')]-indolenine, 2,3,3-trimethyl-5-[5'-methylsulphonylamino-benzoxazolyl-(2')]-indolenine, 2,3,3-trimethyl-5-[5'-benzylsulphonyl-benzoxazolyl-(2')]-indolenine, 2,3,3-trimethyl-5-[5'-β-methoxyethyl-benzoxazolyl-(2')]-indolenine, 2,3,3-trimethyl-5-[5'-diethylaminocarbonyl-benzoxazolyl-(2')]-indolenine, 2,3,3-trimethyl-5-[-5'-methoxycarbonyl-benzoxazolyl-)2')]-indolenine, 2,3,3-trimethyl-5-[5'-β-methoxy-ethoxycarbonyl-benzoxazolyl-(2')]-indolenine, 2,3,3-trimethyl-5-[5'-propionylamino-benzoxazolyl-(2')]-indolenine, 2,3,3-trimethyl-5-[5', 6'-tetramethylene-benzoxazolyl-(2')]-indolenine, 2,3,3-trimethyl-5-[5', 6'-trimethylene- benzoxazolyl-(2')]-indolenine, 2,3,3-trimethyl-5-naphth(1,2-d)-oxazolyl-(2')-indolenine, 2,3,3-trimethyl-5oxaxolo(5,4-b)-pyridine-(2')-indolenine, 2,3,3-trimethyl-5-oxazolo(4,5-g)-quinoline-(2')-indolenine, 2,3,3-trimethyl-5-oxazolo(4,5-c)-quinoline-(2')-indolenine, 2,3,3-trimethyl-5-oxazolo(4,5-d)-pyridazine-(2')-indolenine, 2,3,3-trimethyl-5-oxazolo(4,5-d)-quinoxaline-(2')-indolenine, 2,3,3-trimethyl-5-oxazolo(5,4-d)-pyrimidine-(2')-indolenine, 2,3,3-trimethyl-5-acenaphth(5,4-d)-oxazolyl-(8')-indolenine, 2,3,3-trimethyl-5-benzimidazolyl-(2')-indolenine, 2,3,3-trimethyl-5-[1'-methyl-benzimidazolyl-(2')]-indolenine, 2 -methyl-3,3-diethyl-5-[1'-ethyl-5'-methyl-benzimidazolyl-(2')]-indolenine, 2,3,3-trimethyl-5-[5'-ethoxy-benzimidazolyl-(2')]-indolenine, 2,3,3-trimethyl-5-imidazolo-(5,4-d)pyrimidine-(2')-indolenine, 2,3,3-trimethyl-5-[6'-methyl-benzthiazolyl-(2')]-indolenine, 2,3,3-trimethyl-5[6'-methoxy-benzthiazolyl-(2')]-indolenine and 2,3,3-trimethyl-5-[5'-chloro-benzthiazolyl-(2')]-indolenine.

The azolindiolenines of the formula (II) required as the starting material are for example accessible by condensation of appropriate indolenine-5-carboxylic acids or of their derivatives with o-amino compounds of the formula

wherein

A and X have the abovementioned meaning, under the customary conditions of the azole synthesis.

Instead of the azole-5-carboxylic acids, it is also possible to condense the corresponding indolenine-5-aldehydes with the o-amino compounds of the formula (VI), but in that case it is necessary to subject the corresponding azomethines to a cyclising dehydrogenation in a manner which is in itself known, by means of oxidising agents, such as cupric sulphate, lead tetraacetate, nitrobenzene or chloranil.

A second method of manufacture by which the compounds of the formula (II) are accessible consists of the reacting azolylphenylhydrazines of the formula

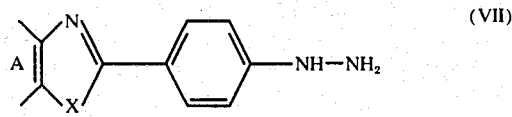

in which

A and X have the abovementioned meaning, with ketones of the formula

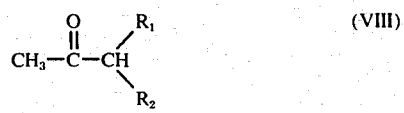

in which $R_1$ and $R_2$ have the abovementioned meaning,
in the presence of zinc chloride, at elevated temperatures, in a manner which is in itself known.

Suitable alkylating agents and aralkylating agents for the conversion, according to the invention, of compounds of the formula (II) into those of the formula (III) are, for example, alkyl halides, such as methyl iodide, ethyl bromide, n-propyl bromide, i-propyl chloride, alkyl bromide, n-butylbromide and isoamyl chloride, sulphuric acid esters of lower alkanols, such as dimethyl sulphate or diethyl sulphate, aromatic sulphonic acid esters, such as p-toluenesulphonic acid methyl ester and ethyl ester, and m-chlorobenzenesulphonic acid ethyl ester, and substituted alkyl halides, such as β-chloropropionitrile; 4-hydroxybutyl bromide, phenylethyl bromide benzyl chloride, p-chlorobenzyl chloride, p-methoxybenzyl chloride, p-cyanobenzyl chloride, phenylacyl chloride, chloroacetic acid methyl ester, 62-chloropropionic acid ethyl ester and β-bromopropionic acid dimethylamide. Dimethyl sulphate and diethyl sulphate are particularly preferred.

The liberation of the azolindolenine-methylene bases of the formula (VI) from the corresponding salts of the formula (III) is achieved in a manner which is in itself known by dissolving the salts of the formula (III), for example in water, and precipitating the methylene base by adding alkali.

The new methylene bases of the formula (IV) are distinguished in that in contrast to most known 1,3,3-trimethyl-2-methylene-indolines they are not obtained as oils which are sensitive to air, but as crystalline substances of relatively good stability, and can hence be isolated particularly easily and conveniently processed further.

The methylene bases of the formula IV can be converted in accordance with formylating methods which are in themselves known into the azolindoline-ω-aldehydes of the formula (V), according to the invention. This reaction can be carried out particularly simply and smoothly if the formylation is carried out according to the Vilsmeier method. Suitable Vilsmeier formylating mixtures are for example obtained if phosphorus oxychloride, phosgene or thionyl chloride are reacted with tertiary formamides, such as dimethylformamide or N-formyl-N-methyl-aniline; a mixture of equimolar amounts of phsophorus oxychloride and dimethylformamide is preferred. Excess dimethylformamide or acetonitrile can for example serve as the solvent and diluent. The reaction temperatures can be varied over a major range without the result being changed significantly. The process is advantageously carried out at between 30° and 85° C. preferably at 35°–60° C.

The azolindolines of the formula (I) are valuable new intermediate products for methine dyestuffs, which are distinguished by particularly high colour strength, high clarity, excellent affinity, outstanding fastness to sublimation and very good fastness to light, rubbing, perspiration and washing, these being properties which the methine dyestuffs hitherto proposed do not possess to the same extent.

A particularly valuable class of azolindolines within the framework of the formula (I) corresponds to the formula

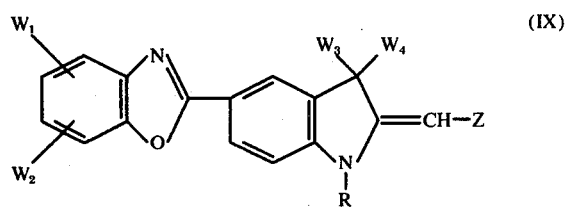

wherein
$W_1$ represents hydrogen, alkyl, cyclohexyl, phenyl, chlorine, alkoxy, alkylsulphonyl, dialkylaminosulphonyl, alkoxycarbonyl or acylamino and
$W_2$ represents hydrogen or alkyl, with the alkyl and alkoxy radicals having 1 to 5 C atoms, and
$W_1$ and $W_2$ can additionally together represent the remaining members of a fused 5-membered or 6-membered cycloaliphatic ring or of a benzene ring,
$W_3$ and $W_4$ independently of one another represent methyl or ethyl groups,
R denotes an alkyl radical and
Z denotes hydrogen or an aldehyde group.

A further object of the present invention are azolindoline dyestuffs of the general formula

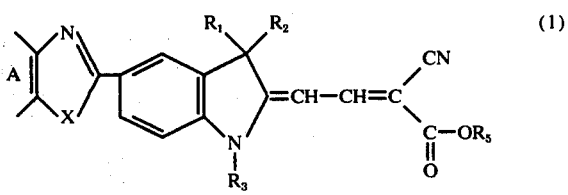

wherein
$R_1$ and $R_2$ denote alkyl radicals or represent the remaining members of a cycloalkyl radical,
$R_3$ denotes an alkyl or aralkyl radical,
$R_5$ denotes an alkyl or aralkyl radical,
X represents oxygen, sulphur or $=NR_4$,
wherein
$R_4$ denotes hydrogen or an alkyl, cycloalkyl or aralkyl radical, and
A represents the remaining members of an aromatic radical,
as well as processes for their manufacture and their use.

The more exact meaning of the radicals $R_1$, $R_2$, $R_3$, $R_4$ and A has been given above.

Amongst the alkyl radicals $R_5$, there should preferably be mentioned those with 1 to 5 C atoms, which can possess further substituents, such as halogen, hydroxyl, alkoxy and nitrile. Suitable alkyl radicals of this nature are, for example, methyl, ethyl, chloroethyl, hydroxyethyl, methoxyethyl, cyanoethyl, n-propyl, isopropyl, and n-, i- and t-butyl, and allyl.

Suitable aralkyl radicals $R_5$ are especially the benzyl radical and the phenylethyl radical.

The new azolindoline dyestuffs of the formula (1) are obtained if aldehydes of the formula

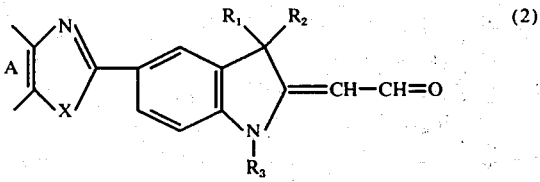

wherein

A, X, R₁, R₂ and R₃ have the abovementioned meaning, are condensed with a cyanoacetic acid ester of the formula

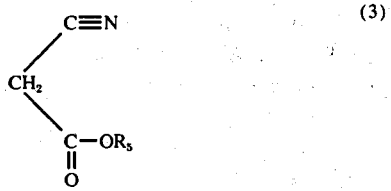

wherein

R₅ has the abovementioned meaning.

The condensation is carried out in the presence or absence of a solvent or diluent, preferably with the addition of an alkaline catalyst, at elevated temperature, preferably in the range of 60°– 120° C.

Suitable solvents or diluents are those which are inert under the conditions of the condensation and are capable of adequately dissolving the reactants, and from which the reaction products separate out well. For example, methanol, ethanol, 2-methoxyethanol, isopropanol, dioxane, benzene, toluene, chlorobenzene, chloroform and pyridine are used.

As alkaline catalysts, sodium hydroxide, potassium carbonate and sodium acetate should for example be mentioned, secondary organic bases, such as diethylamine, and especially pyrrolidine or piperidine, being preferred.

The reactants can be employed in a molar ratio, but an approximately 5% excess of the cyanoacetic acid ester component (3) is advantageous. It is also possible to choose a larger excess of cyanoacetic ester without thereby having an adverse effect on the course of the reaction.

Suitable aldehydes of the formula (2) are, for example: 1,3,3-trimethyl-5-[5′-methyl-benzoxazolyl-(2′)]-2-methylene-indoline-ω-aldehyde, 1-ethyl-3,3-dimethyl-5-[5′-chlorobenzoxazolyl-(2)]-2-methylene-indoline-ω-aldehyde, 1-chloroethyl-3,3-dimethyl-5-[5′-trifluoromethyl-benzoxazolyl-(2′)]-2-methylene-indoline-ω-aldehyde, 1-n-propyl-3,3-dimethyl-5-[5′-cyclohexyl-benzoxazolyl-(2′)]-2-methylene-indoline-ω-aldehyde, 1-allyl-3,3-dimethyl-5-[5′-phenyl-benzoxazolyl-(2′)]-2-methylene-indoline-ω-aldehyde, 1-n-butyl-3,3-dimethyl-5-[5′-methoxy-benzoxazolyl-(2′)]-2-methylene-indoline-ω-aldehyde, 1-methyl-3,3-pentamethylene-5-benzoxazolyl-(2′)-2-methylene-indoline-ω-aldehyde, 1-cyanoethyl-3,3-dimethyl-5-[5′,6′-dimethyl-benzoxazolyl-(2′)]-2-methylene-indoline-ω-aldehyde, 1-benzyl-3,3-dimethyl-5-[5′-bromobenzoxazolyl-(2′)]-2-methylene-indoline-ω-aldehyde, 1-β-phenylethyl-3,3-diethyl-5-[5′-tertiary-butyl-benzoxazolyl-(2′)]-2-methylene-indoline-ω-aldehyde, 1-p-chlorobenzyl-3,3-dimethyl-5-[5′-fluoro-benzoxazolyl-(2′)]-2-methylene-indoline-ω-aldehyde, 1-methoxycarbonylmethyl-3,3-dimethyl-5-[5′-ethylbenzoxazolyl-(2′)]-2-methylene-indoline-ω-aldehyde, 1-β-ethoxycarbonylethyl-3,3-dimethyl-5-[5′-ethylsulphonyl-benzoxazolyl-(2′)]-2-methylene-indoline-ω-aldehyde, 1-β-dimethylaminocarbonylethyl-3,3-dimethyl-5-[5′-dimethylaminosulphonyl-benzoxazolyl-(2′)]-2-methylene-indoline-ω-aldehyde, 1′,3,3-trimethyl-5-[5′-β-bromoethyl-benzoxazolyl-(2′)]-2-methylene-indoline-ω-aldehyde, 1,3,3-trimethyl-5-[5′-acetylamino-benzoxazolyl-(2′)]-2-methylene-indoline-ω-aldehyde, 1,3,3-trimethyl-5-[5′-chloroethyl-benzoxazolyl-(2′)]-2-methylene-indoline-ω-aldehyde, 1,3,3-trimethyl-5-[5′-benzyl-benzoxazolyl-(2′)]-2-methylene-indoline-ω-aldehyde, 1,3,3-trimethyl-5-[5′-β-phenylethyl-benzoxazolyl-(2′)]-2-methylene-indoline-ω-aldehyde, 1,3,3-trimethyl-5-[5′-methoxycarbonyl-benzoxazolyl-(2′)]-2-methylene-indoline-ω-aldehyde, 1,3,3-trimethyl-5-[5′-dimethylamino-carbonyl-benzoxazolyl-(2′)]-2-methylene-indoline-ω-aldehyde, 1,3,3-trimethyl-5-[5′-β-methoxy-ethoxycarbonyl-benzoxazolyl-(2′)]-2-methylene-indoline-ω-aldehyde, 1,3,3-trimethyl-5-[5′,6′-tetramethylene-benzoxazolyl-(2′)]-2-methylene-indoline-ω-aldehyde, 1,3,3-trimethyl-5-[5′,6′-trimethylene-benzoxazolyl-(2′)]-2-methylene-indoline-ω-aldehyde, 1,3,3-trimethyl-5-naphth(1,2-d)oxazolyl-(2′)-2-methylene-indoline-ω-aldehyde, 1,3,3-trimethyl-5-oxazolo(5,4-b)pyridine-(2′)-2-methylene-indoline-ω-aldehyde, 1,3,3-trimethyl-5-oxazolo(4,5-g)-quinoline-(2′)-2-methylene-indoline-ω-aldehyde, 1,3,3-trimethyl-5-oxazolo(4,5-d)pyridazine-(2′)-2-methylene-indoline-ω-aldehyde, 1,3,3-trimethyl-5-oxazolo(4,5-d)quinoxaline-(2′)-2-methylene-indoline-ω-aldehyde, 1,3,3-trimethyl-5-oxazolo-(5,4-d)pyrimidine-(2′)-2-methylene-indoline-ω-aldehyde, 1,3,3-trimethyl-5-acenaphth(5,4-d)oxazolyl-(8′)-2-methylene-indoline-ω-aldehyde, 1,3,3-trimethyl-5-[1′-methyl-benzimidazolyl-(2′)]-2-methylene-indoline-ω-aldehyde, 1,3,3-triethyl-5-[1′-β-cyanoethyl-5′-methyl-benzidimidazolyl-(2′)]-2-methylene-indoline-ω-aldehyde, 1,3,3-trimethyl-5-[5′-ethoxy-1′-ethyl-benzimidazolyl-(2′)]-2-methylene-indoline-ω-aldehyde, 1,3,3-trimethyl-5-imidazolo(5,4-d)pyrimidine-(2′)-2-methylene-indoline-ω-aldehyde, 1,3,3-trimethyl-5-[6′-methyl-benzthiazolyl-(2′)]-2-methylene-indoline-ω-aldehyde, 1,3,3-trimethyl-5-[6′-methoxy-benzthiazolyl-(2′)]-2-methylene-indoline-ω-aldehyde and 1,3,3-triethyl-5-[5′-chloro-benzthiazolyl-(2′)]-2-methylene-indoline-ω-aldehyde.

Suitable cyanoacetic acid esters of the formula (3) are, for example: cyanoacetic acid methyl ester, cyanoacetic acid ethyl ester, cyanoacetic acid β-methoxyethyl ester, cyanoacetic acid β-chloroethyl ester, cyanoacetic acid β-cyanoethyl ester, cyanoacetic acid β-hydroxyethyl ester, cyanoacetic acid n-propyl ester, cyanoacetic acid isopropyl ester, cyanoacetic acid allyl ester, cyanoacetic acid n-butyl ester, cyanoacetic acid isobutyl ester, cyanoacetic acid isoamyl ester, cyanoacetic acid benzyl ester, cyanoacetic acid β-phenylethyl ester and cyanoacetic acid p-methoxy-benzyl ester.

A particularly valuable class of azolindoline dyestuffs within the framework of the formula (1) corresponds to the formula

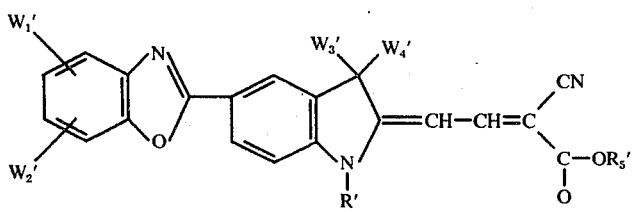

wherein
- W₁' represent hydrogen, alkyl, cyclohexyl, phenyl, chlorine, alkoxy, alkylsulphonyl, dialkylaminosulphonyl, alkoxycarbonyl or acylamino and
- W₂' represents hydrogen or alkyl, with the alkyl and alkoxy radicals having 1–5 C atoms, and wherein
- W₁' and W₂' can additionally together represent the remaining members of a fused 5-membered or 6-membered cycloaliphatic ring or of a benzene ring,
- W₃' and W₄' independently of one another represent methyl or ethyl groups,
- Z denotes hydrogen or an aldehyde group and
- R' and R₅' each individually denote an alkyl radical with 1–5 C atoms.

The new azolindoline dyestuffs of the formula (1) are in particular suitable for dyeing and printing synthetic fibre materials and fabric materials such as, for example, polyesters, but preferably materials of synthetic polyamides and polyurethanes.

These dyestuffs produce, on the fibers and fabrics mentioned, extraordinarily brilliant dyeings in yellow shades, which are distinguished by particularly high colour strength, very good build-up capacity and affinity and excellent fastness properties, such as fastness to washing, rubbing, sublimation, perspiration, exhaust gas and light.

The yellow dyestuffs hitherto proposed do not possess these advantageous properties to the same extent. As against the nearest comparable dyestuffs (German Patent Specification No. 1,172,387 and French Patent Specification No. 1,460,912), the significantly higher colour strength, the better clarity of shade, the better affinity and the better fastness to sublimation on polyamides should be singled out.

The new dyestuffs of the formula (1) can be used for dyeing and printing in accordance with customary processes, for example in the form of aqueous dispersions or printing pastes. The dyebaths and printing pastes can contain the customary dyeing auxiliary additives, such as levelling agents, dispersing agents and dyeing accelerators.

The new dyestuffs can also be dyed advantageously from organic solutions, for example from solutions in which solvents which are immiscible with water are used, such as tetrachloroethylene, trichloroethylene, 1,1,2-trichloroethane or 1,1,1-trichloropropane.

The parts indicated in the Examples which follow are parts by weight unless otherwise indicated, and the degrees of temperature indicated are degrees centigrade.

EXAMPLE 1a

A mixture of 260 parts of 3-amino-4-hydroxy-toluene, 406 parts of 2,3,3-trimethyl-indolenine-5-carboxylic acid and 20 parts of boric acid is heated for 1 hour to 180°–190° in a slight stream of nitrogen, whilst distilling off some liquid, and is subsequently heated for a further 40 minutes to 230°. The melt is then fractionally distilled in vacuo, whereupon first of all the water formed and excess 3-amino-4-hydroxy-toluene pass under a waterpump vacuum. Thereafter, the following fractions are obtained:

First runnings: 30 parts, 130°–170°/2.5 mm Hg.
Main fraction: 420 parts, 170°–240°/0.1 mm Hg (bath temperature not exceeding 270°).

The main fraction solidifies in the receiver to give a yellowish, crystalline mass and can be further processed without additional purification. A sample recrystallised from alcohol melts at 160°–162° and corresponds to the formula

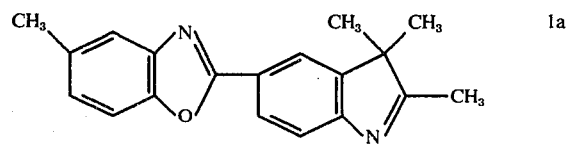

Using the appropriate starting materials, the following compounds are obtained analogously: 2,3,3-trimethyl-5-[5'-chloro-benzoxazolyl-(2')]-indolenine, 2-methyl-3,3-diethyl-5-[5'-trifluoromethyl-benzoxazolyl-(2')]-indolenine, 2,3-dimethyl-3-ethyl-5-[5'-cyclohexyl-benzoxazolyl-(2')]-indolenine, 2,3,3-trimethyl-5-[5'-phenyl-benzoxazolyl-(2')]-indolenine, 2,3,3-trimethyl-5-[5'-methoxy-benzoxazolyl-(2')]-indolenine, 2,3,3-trimethyl-5-[5',6'-dimethyl-benzoxazolyl-(2')]-indolenine, 2,3,3-trimethyl-5-[5'-bromobenzoxazolyl-(2')]-indolenine, 2,3,3-trimethyl-5-[5'-tertiary-butyl-benzoxazolyl-(2')]-indolenine, 2,3,3-trimethyl-5-[5'-fluorobenzoxazolyl-(2')]-indolenine, 2,3,3-trimethyl-5-[5'-ethyl-benzoxazolyl-(2')]-indolenine, 2,3,3-trimethyl-5-[5'-ethyl-sulphonyl-benzoxazolyl-(2')]-indolenine, 2,3,3-trimethyl-5-[5'-dimethylaminosulphonyl-benzoxazolyl-(2')]-indolenine, 2,3,3-trimethyl-5-[5'-β-bromoethyl-benzoxazolyl-(2')]-indolenine, 2,3,3-trimethyl-5-[5'-acetylamino-benzoxazolyl-(2')]-indolenine, 2,3,3-trimethyl-5-[5'-β-hydroxyethyl-benzoxazolyl-(2')]-indolenine, 2,3,3-trimethyl-5-[5'-benzyl-benzoxazolyl-(2')]-indolenine, 2-methyl-3,3-pentamethylene-5-benzoxazolyl-(2')-indolenine, 2,3,3-trimethyl-5-[5'-β-phenylethyl-benzoxazolyl-(2')]-indolenine, 2,3,3-trimethyl-5-[5'-β-chloroethyl-benzoxazolyl-(2')]-indolenine, 2,3,3-trimethyl-5-[5'-methylsulphonyl-benzoxazolyl-(2')]-indolenine, 2,3,3-trimethyl-5-[5'-diethylaminosulphonyl-benzoxazolyl-(2')]-indolenine, 2,3,3-trimethyl-5-[5'-methylsulphonylamino-benzoxazolyl-(2')]-indolenine, 2,3,3-trimethyl-5-[5'-benzylsulphonyl-benzoxazolyl-(2')]-indolenine, 2,3,3-trimethyl-5-[5'-β-methoxyethyl-benzoxazolyl-(2')]-indolenine, 2,3,3-trimethyl-5-[5'-diethylaminocarbonyl-benzoxazolyl- (2')]-indolenine, 2,3,3-trimethyl-5-[5'-methoxycarbonyl-benzoxazolyl-(2')]-indolenine, 2,3,3-trimethyl-5-[5'-β-methoxy-ethoxycarbonyl-benzoxazolyl-(2')]-indolenine, 2,3,3-trimethyl-5-[5'-propionylamino-benzoxazolyl-(2')]-indolenine, 2,3,3-trimethyl-5-[5', 6'-tetramethylene-benzoxazolyl-(2')]-indolenine, 2,3,3-trimethyl-5-[5', 6'-triethylene-benzoxazolyl-(2')]-indolenine, 2,3,3-trimethyl-5-naphth(1,2-d)oxazolyl-(2')-indolenine, 2,3,3-trimethyl-5-oxazolo(5,4-b)pyridine-(2')-indolenine, 2,3,3-trimethyl-5-oxazolo(4,5-g)quinoline-(2')-indolenine, 2,3,3-trimethyl-5-oxazolo(4,5-c)quinoline-(2')-indolenine, 2,3,3-trimethyl-5-oxazolo(4,5-d)pyridazine-(2')-indolenine, 2,3,3-trimethyl-5-oxazolo(4,5-d)quinoxaline-(2')-indolenine, 2,3,3-trimethyl-5-oxazolo(5,4-d)pyrimidine-(2')-indolenine, 2,3,3-trimethyl-5-acenaphth(5,4-d)oxazolyl-(8')-indolenine, 2,3,3-trimethyl-5-benzimidazolyl-(2')-indolenine, 2,3,3-trimethyl-5-[1'-methyl-benzimidazolyl-(2')]-indolenine, 2-methyl-3,3-diethyl-5-[1'-ethyl-5'-methyl-benzimidazolyl-(2')]-indolenine, 2,3,3-trimethyl-5-[5'-ethoxy-benzimidazolyl-(2')]-indolenine, 2,3,3-trimethyl-5-imidazolo(5,4-d)pyrimidine-(2')-indolenine, 2,3,3-trimethyl-5-[6'-methyl-benzthiazolyl-(2')]-indolenine, 2,3,3-trimethyl-5-[6'-methoxy-benzthiazolyl-(2')]-indolenine an 2,3,3-trimethyl-5-[5'-chloro-benzthiazolyl-(2')]-indolenine.

EXAMPLE 2a 419.5 parts of the compound of the formula 1a (main fraction of Example 1a) are dissolved in 2700 parts by volume of chlorobenzene, with warming. 200 parts by volume of chlorobenzene are then distilled off in a waterpump vacuum. Thereafter 181 parts of dimethyl sulphate are added dropwise at 50° to 60°, without further heating, and occasional short cooling with cold water may be necessary. When the exothermic reaction has subsided, the batch is further heated to 55°-60° for 3 hours. After cooling, the crystalline precipitate is filtered off and washed with about 400 parts by volume of chlorobenzene. The resulting compound of the formula

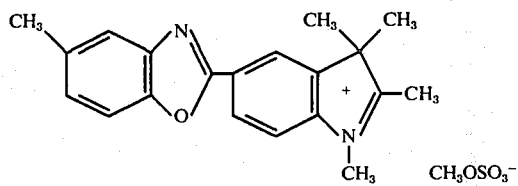

can be further processed whilst moist with chlorobenzene. If the substance is dried in vacuo at 70° in order to determine the yield, 470 parts of melting point 184°-192° (decomposition) are obtained. A sample of the substance manufactured from recrystallised intermediate product melts at 283°, with decomposition.

Thereafter, the quaternary salt which is moist with chlorobenzene is dissolved in 5400 parts of water at 40° and the chlorobenzene is distilled off azeotropically in vacuo, until the distillate which passes over is no longer cloudy. The solution is subsequently clarified at 40° with 15 parts of active charcoal, and is filtered. 740 parts of 25% strength sodium hydroxide solution are slowly run into the filtrate, whilst stirring, whereupon an almost colourless, crystalline precipitate separates out. This is filtered off, washed with water until neutral and dried in vacuo at 50°. 243 parts of the compound of the formula

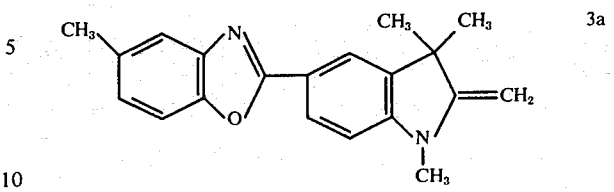

of melting point 153°-156° (decomposition) are obtained. Dilute solutions of the substance in organic solvents, such as alcohol, toluene or dimethylformamide show a strong blue fluorescence. In contrast to most known 1,3,3-trimethyl-2-methylene-indolines, this compound has relatively good stability to atmospheric oxygen.

If, instead of dimethyl sulphate, an equimolar amount of diethyl sulphate is employed and the quaternisation is carried out for 10 hours at 70°, then the compound of the formula

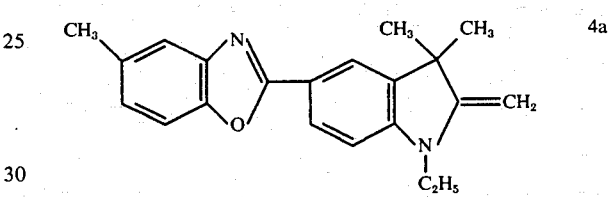

is obtained in comparable yield after working up under alkaline conditions. If the quaternisation is carried out with p-toluenesulphonic acid methyl ester, p-toluenesulphonic acid ethyl ester or m-chlorobenzenesulphonic acid methyl ester, a reaction temperature of 100°-120° is required.

Quaternisations of 1a with n-propyl bromide, i-propyl chloride, allyl bromide, n-butyl bromide, isoamyl chloride, chloropropionitrile, chloroacetic acid methyl ester, β-chloropropionic acid ethyl ester and benzyl chloride are carried out in an autoclave at 120°-160°.

Using the appropriate starting materials, the following compounds are obtained analogously: 1)]-3,3-dimethyl-5-[5'-chloro-benzoxazolyl-(2')]-2-methylene-indoline, 1-ethyl-3,3-dimethyl-5-[5'-cyclohexyl-benzoxazolyl-(2')]-2-methylene-indoline, 1,3,3-trimethyl-5-[5'-phenyl-benzoxazolyl-(2')]-2-methylene-indoline, 1,3,3-trimethyl-5-[5'-methoxy-benzoxazolyl-(2')]-2-methylene-indoline, 1,3,3-trimethyl-5-[5'-bromobenzoxazolyl-(2')]-2-methylene-indoline, 1-ethyl-3,3-dimethyl-5-[5',6'-dimethyl-benzoxazolyl-(2')]-2-methylene-indoline, 1,3,3-trimethyl-5-[5'-tertiary-butyl-benzoxazolyl-(2')]-2-methylene-indoline, 1,3,3-trimethyl-5[5'-fluoro-benzoxazolyl-(2')]-2-methylene-indoline, 1,3,3-trimethyl-5-[5'-ethyl-benzoxazolyl-(2')]2-methylene-indoline, 1-ethyl-2,3-dimethyl-5-[5'-ethylsulphonyl-benzoxazolyl-(2')]-2-methylene-indoline, 1,3,3-trimethyl-5-[5'-dimethylaminosulphonyl-benzoxazolyl-(2')]-2-methylene-indoline, 1,3,3-trimethyl-5-[5'-methoxycarbonyl-benzoxazolyl-()]-2-methylene-indoline, 1,3,3-trimethyl-5-[5'-benzyl-benzoxazolyl-(2')]-2-methylene-indoline, 1,3,3-trimethyl-5-[5'-diethylaminocarbonyl-benzoxazolyl-(2')]-2-methylene-indoline, 1,3,3-trimethyl-5-[5',6'-tetramethylene-benzoxazolyl-(2')]-2-methylene-indoline, 1,3,3-trimethyl-5-[5',6'-trimethylenebenzoxazolyl-(2')]-2-methylene-indoline, 1,3,3-triethyl-5-benzoxazolyl-(2')-2-methylene-indoline, 1-methyl-3,3-pentamethylene-5-benzoxazolyl-(2')-2-methylene-indoline, 1,3,3-trimethyl-5-[5'-acetylamino-benzoxazolyl-(2')]-2-methylene-indoline, 1,3,3-trimethyl-5-[5'-isopropyl-benzoxazolyl-(2')]-2-methylene-indoline, 1,3,3-trimethyl-5-[5'-(1'',1'',3'',3''-tetramethyl-n-butyl)- benzoxazolyl-(2')]-2-methylene-indoline, 1,3,3-trimethyl-5-[5'-ethoxy-benzoxazolyl-(2')]-2-methylene-indoline, 1,3,3-trimethyl-5-[5'-methylaminosulphonyl-benzoxazolyl-(2')]-2-methylene-indoline, 1,3,3-trimethyl-5-[5'-n-propylaminocarbonyl-benzoxazolyl-(2')]-2-methylene-indoline, 1,3,3-trimethyl-5-naphth(1,2-d)oxazolyl-(2') -2-methylene-indoline, 1,3,3-trimethyl-5-oxazolo(5,4-b)-pyridine-(2')-2-methylene-indoline, 1,3,3-trimethyl-5-oxazolo-(4,5-g)-quinoline-(2')-2-methylene-indoline, 1,3,3-trimethyl-5-oxazolo(4,5-d)pyridazine-(2')-2-methylene-indoline, 1,3,3-trimethyl-5-oxazolo(4,5-d)quinoxaline-(2')-2-methylene-indoline, 1,3,3-trimethyl-5-oxazolo(5,4-d)pyrimidine-(2')-2-methylene-indoline, 1,3,3-trimethyl-5-acenaphth(5,4-d)-oxazolyl-(8')-2-methylene-indoline, 1.3,3-trimethyl-5-[1'-methyl-benzimidazolyl-(2')]-2-methylene-indoline, 1,3,3-trimethyl-5-[1'-β-cyanoethyl-5'-methyl-benzimidazolyl-(2')]-2-methylene-indoline, 1,3,3-trimethyl-5-[5'ethoxy-1'-ethyl-benzimidazolyl-(2')]-2-methylene-indoline, 1,3,3-trimethyl-5-[6'-methyl-benzthiazolyl-(2')]-2-methylene-indoline, 1,3,3-trimethyl-5-[6'-methoxy-benzthiazolyl-(2')]-2-methylene-indoline and 1,3,3-trimethyl-5-[5'-chloro-benzthiazolyl-(2')]-2-methylene-indoline.

EXAMPLE 3a 130 g of dimethylformamide are rapidly added dropwise to 150 parts of phosphorus oxychloride at 25° to 50°, whilst cooling with water. The mixture is further warmed to 50° for 1 hour and is treated with 400 parts of acetonitrile. Thereafter 242 parts of the compound of the formula 3a are added over the course of 20 minutes at 50°–70°, whilst gently cooling with water and stirring, and the reaction mixture is heated for 2 hours to 50° and 4 hours to 70° and poured out, whilst stirring, onto a mixture of 1500 parts of water, 1000 parts of ice and 560 parts of 50% strength sodium hydroxide solution. The mixture is stirred for 5 hours. The crystalline precipitate which forms is then filtered off, washed with water until neutral and dried in vacuo at 70°. 249 parts of the compound of the formula

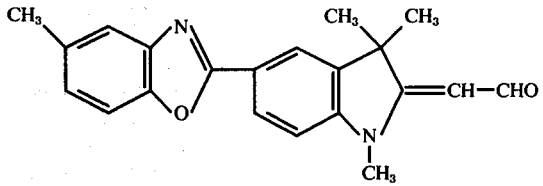

of melting point 239°–241° are obtained.

If the reaction mixture is not poured out onto ice water and sodium hydroxide solution, but only onto ice water, a strongly acid, aqueous solution of the Vilsmeier intermediate product of the formula

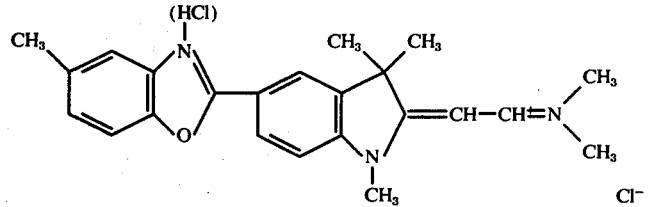

is obtained.

If, instead of the compound of the formula 3a, an equimolar amount of the compound of the formula 4a is employed, 259 parts of the compound of the formula

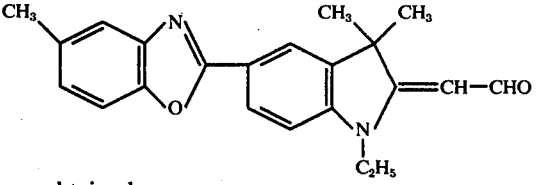

are obtained.

The following compounds are obtained analogously from the appropriate starting components: 1-ethyl-3,3-dimethyl-5-[5'-chloro-benzoxazolyl-(2')]-2-methylene-indoline-ω-aldehyde, 1-ethyl-3,3-dimethyl-5-[5'-cyclohexyl-benzoxazolyl-(2')]-2-methylene-indoline-ω-aldehyde, 1,3,3-trimethyl-5-[5'-phenyl-benzoxazolyl-(2')]-2-methylene-indoline-ω-aldehyde, 1,3,3-trimethyl-5-[5'-methoxy-benzoxazolyl-(2')]-2-methylene-indoline-ω-aldehyde, 1,3,3-trimethyl-5-[5'-bromo-benzoxazolyl-(2')]-2-methylene-indoline-ω-aldehyde, 1-ethyl-3,3-dimethyl-5-[5',6'-dimethyl-benzoxazolyl-(2')]-2-methylene-indoline-ω-aldehyde, 1,3,3-trimethyl-5-[5'-tertiary-butyl-benzoxazolyl-(2')]-2-methylene-indoline-ω-aldehyde, 1,3,3-trimethyl-5-[5'-fluoro-benzoxazolyl-(2')]-2-methylene-indoline-ω-aldehyde, 1,3,3-trimethyl-5-[5'-ethyl-benzoxazolyl-(2')-2-methylene-indoline-ω-aldehyde, 1-ethyl-2,3-dimethyl-5-[5'-ethylsulphonyl-benzoxazolyl-(2')]-2-methylene-indoline-ω-aldehyde, 1,3,3-trimethyl-5-[5'-dimethylaminosulphonyl-benzoxazolyl-(2')]-2-methylene-indoline-ω-aldehyde, 1,3,3-trimethyl-5-[5'-methoxycarbonyl-benzoxazolyl-(2')]-2-methylene-indoline-ω-aldehyde, 1,3,3-trimethyl-5-[5'-benzyl-benzoxazolyl-(2')]-2-methylene-indoline-ω-aldehyde, 1,3,3-trimethyl-5-[5'-diethyl-aminocarbonyl-benzoxazolyl-(2')]-2-methylene-indoline-ω-aldehyde, 1,3,3-trimethyl-5-[5',6'-tetramethylene-benzoxazolyl-(2')]-2-methylene-indoline-ω-aldehyde, 1,3,3-trimethyl-5-[5',6'-trimethylene-benzoxazolyl-(2')]-2-methyleneindoline-ω-aldehyde, 1,3,3-triethyl-5-benzoxazolyl-(2')-2-methylene-indoline-ω-aldehyde, 1-methyl-3,3-pentamethylene-5-benzoxazolyl-(2')-2-methylene-indoline-ω-aldehyde, 1,3,3-trimethyl-5-[5'-acetylamino-benzoxazolyl-(2')]-2-methylene-indoline-ω-aldehyde, 1,3,3-trimethyl-5-[5'-isopropyl-benzoxazolyl-(2')]-2-methylene-indoline-ω-aldehyde, 1,3,3-trimethyl-5-[5'-(1'',1'',3'',3''-tetramethyl-n-butyl)-benzoxazolyl-(2')]-2-methylene-indoline-ω-aldehyde, 1,3,3-trimethyl-5-[5'-ethoxy-benzoxazolyl-(2')]-2-methylene-indoline-ω-aldehyde, 1,3,3-trimethyl-5-[5'-methyl-aminosulphonyl-benzoxazolyl-(2')]-2-methylene-indoline-ω-aldehyde, 1,3,3-trimethyl-5-[5'-n-propylaminocarbonyl-benzoxazolyl-(2')]-2-methylene-indoline-ω-aldehyde, 1,3,3-trimethyl-5-naphth(1,2-d)oxazolyl-(2')-2-methylene-indoline-ω-aldehyde, 1,3,3-trimethyl-5-oxazolo(5,4-b)pyridine-(2')-2-methylene-indoline-ω-aldehyde, 1,3,3-trimethyl-5-oxazolo(4,5-g)quinoline-(2')-2-methylene-indoline-ω-aldehyde, 1,3,3-trimethyl-5-oxazolo(4,5-d)pyridazine-(2')-2-methylene-indoline-ω-aldehyde, 1,3,3-trimethyl-5-oxazolo(4,5-d)-quinoxaline-(2')-2-methylene-indoline-ω-aldehyde, 1,3,3-trimethyl-5-oxazolo(5,4-d)pyrimidine-(2')-2-methylene-indoline-ω-aldehyde, 1,3,3-trimethyl-5-acenaphth(5,4-d)oxazolyl-(8')-2-methylene-indoline-ω-aldehyde, 1,3,3-trimethyl-5-[1'-methyl-benzimidazolyl-(2')]-2-methylene-indoline-ω-aldehyde, 1,3,3-trimethyl-5-[1'-β-cyanoethyl-5'-methyl-benzimidazolyl-(2')]-2-methylene-indoline-ω-aldehyde, 1,3,3-trimethyl-5-[5'-ethoxy-1'-ethyl-benzimidazolyl-(2')]-2-methylene-indoline-ω-aldehyde, 1,3,3-trimethyl-5-[6'-methyl-benzthiazolyl-(2')]-2-methylene-indoline-ω-aldehyde, 1,3,3-trimethyl-5-[6'-methoxy-benzthiazolyl-(2')]-2-methylene-indoline-ω-aldehyde, 1,3,3-trimethyl-5-[5'-chloro-benzthiazolyl-(2')]-2-methylene-indoline-ω-aldehyde, 1-n-propyl-3,3-dimethyl-5-[5'-methyl-benzoxazolyl-(2')]-2-methylene-indoline-ω-aldehyde, 1-n-butyl-3,3-dimethyl-5-[5'-methyl-benzoxazolyl-(2')]-2-methylene-indoline-ω-aldehyde, 1-β-cyanoethyl-3,3-dimethyl-5-[5'-methyl-benzoxazolyl-(2')]-2-methylene-indoline-ω-aldehyde, 1-methoxycarbonylmethyl-3,3-dimethyl-5-[5'-methyl-benzoxazolyl-(2')]-2-methylene-indoline-ω-aldehyde, 1-β-ethoxycarbonylethyl-3,3-dimethyl-5-[5'-methyl-benzoxazolyl-(2')]-2-methylene-indoline-ω-aldehyde, 1-β-chloroethyl-3,3-dimethyl-5-[5'-methyl-benzoxazolyl-(2')]-2-methylene-indoline-ω-aldehyde, 1-allyl-3,3-dimethyl-5-[5'-methyl-benzoxazolyl-(2')]-2-methylene-indoline-ω-aldehyde and 1-benzyl-3,3-dimethyl-5-[5'-methyl-benzoxazolyl-(2')]-2-methylene-indoline-ω-aldehyde.

EXAMPLE 4a

A mixture of 260 parts of 3-amino-4-hydroxy-toluene, 406 parts of 2,3,3-trimethyl-indolenine-5-carboxylic acid and 20 parts of boric acid is heated for 1 hour to 180° – 190° in a slight stream of nitrogen, whilst distilling off some liquid, and is subsequently further heated to 240° for 40 minutes. Water and excess 3-amino-4-hydroxy-toluene are then distilled off in a waterpump vacuum, under nitrogen, whilst increasing the internal temperature of the melt to 250°. After cooling to 150° under nitrogen, 2800 parts by volume of chlorobenzene are added and in order completely to remove the water azeotropically, 200 parts by volume of chlorobenzene are distilled off. 270 parts of dimethyl sulphate are subsequently added dropwise at 60° – 65°, whilst occasionally cooling with cold water. The batch is subsequently heated to 60° – 65° for a further 7 hours whilst stirring, and is then cooled to room temperature. The crystalline precipitate is washed with about 1000 parts by volume of chlorobenzene and then with 300 parts by volume of benzene, and is dried in vacuo at 50°. 745 g of quaternary salt of the formula 2a, of melting point 196° – 198°, are obtained. These are suspended in 1700 parts by volume of dimethylformamide, whilst stirring. 181 parts of triethylamine are added dropwise at 20° – 25° under nitrogen, whilst cooling, whereupon the methylene base of the formula 3a forms. The mixture is then treated dropwise, at 20° – 55°, with 400 parts of phosphorus oxychloride, whilst stirring and cooling with an icebath. Thereafter the batch is heated to 60° for a further 6 hours, whilst stirring, and is then poured out onto a mixture of 4000 parts of water, 1500 parts of ice and 1550 parts by volume of 50% strength sodium hydroxide solution, whilst stirring. The mixture is stirred for 6 hours at room temperature and the product is filtered off, washed with 6000 parts of water until neutral and dried at 50° in vacuo. 540 parts of aldehyde of the formula 5a are obtained, melting at 240°–242° after recrystallisation from dimethylformamide.

EXAMPLE 1b 102 parts of 1,3,3-trimethyl-5-[5'-methyl-benzoxazolyl-(2')]-2-methylene-indoline-ω-aldehyde (compound 5a in Example 3a), 45 parts of cyanoacetic acid ethyl ester and 10 parts of piperidine in 800 parts by volume of ethanol are heated to the boil for 5 hours under reflux, whilst stirring, and are then cooled. The crystalline precipitate which separates out is filtered off, washed with ice-cold methanol and dried at 50° in vacuo. 120 parts of the compound of the formula

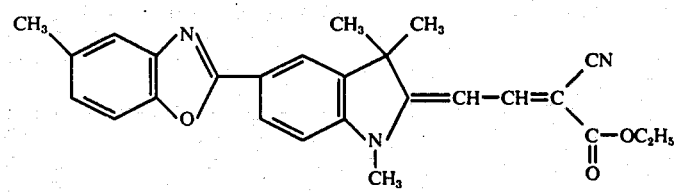

1b melting at 237° to 239° are obtained. Strongly greenish-tinged, clear yellow on polyamide.

The following dyestuffs are obtained analogously, if the appropriate starting materials are used:

Table 1

| No. | U¹ | U² | U³ | U⁴ | U⁵ | U⁶ | Colour shade on polyamide |
|---|---|---|---|---|---|---|---|
| 2b | $CH_3$ | H | $CH_3$ | $CH_3$ | $C_2H_5$ | $CH_3$ | greenish-tinged yellow |
| 3b | Cl | H | $CH_3$ | $CH_3$ | $C_2H_5$ | $-CH_2-CH_2-OCH_3$ | greenish-tinged yellow |
| 4b | cyclohexyl | H | $CH_3$ | $CH_3$ | $C_2H_5$ | $-CH_2-CH_2-CN$ | greenish-tinged yellow |
| 5b | phenyl | H | $CH_3$ | $CH_3$ | $CH_3$ | $-CH_2-CH_2-CH_3$ | greenish-tinged yellow |
| 6b | $CH_3O$ | H | $CH_3$ | $CH_3$ | $CH_3$ | $-CH(CH_3)_2$ | greenish-tinged yellow |
| 7b | H | $CH_3O$ | $CH_3$ | $CH_3$ | $CH_3$ | $-CH_2-CH_2-OH$ | greenish-tinged yellow |
| 8b | Br | H | $CH_3$ | $CH_3$ | $CH_3$ | $-CH_2-CH_2-Cl$ | greenish-tinged yellow |
| 9b | $CH_3$ | $CH_3$ | $CH_3$ | $CH_3$ | $CH_3$ | $-CH_2-CH=CH_2$ | greenish-tinged yellow |
| 10b | $(CH_3)_3C-$ | H | $CH_3$ | $CH_3$ | $CH_3$ | $-CH_2-CH_2-CH_2-CH_3$ | greenish-tinged yellow |
| 11b | F | H | $CH_3$ | $CH_3$ | $CH_3$ | $-CH_2-CH(CH_3)_2$ | greenish-tinged yellow |
| 12b | $C_2H_5-$ | H | $CH_3$ | $CH_3$ | $CH_3$ | $-CH_2-CH_2-CH(CH_3)_2$ | greenish-tinged yellow |
| 13b | $C_2H_5SO_2-$ | H | $CH_3$ | $CH_3$ | $C_2H_5$ | $-CH_2-C_6H_5$ | greenish-tinged yellow |
| 14b | $(CH_3)_2N-SO_2-$ | H | $CH_3$ | $CH_3$ | $CH_3$ | cyclohexyl | greenish-tinged yellow |
| 15b | $CH_3O-C(O)-$ | H | $CH_3$ | $CH_3$ | $CH_3$ | $-CH_2-CH_2-C_6H_5$ | greenish-tinged yellow |
| 16b | $C_6H_5-CH_2-$ | H | $CH_3$ | $CH_3$ | $CH_3$ | $C_2H_5$ | greenish-tinged yellow |
| 17b | $(C_2H_5)_2N-C(O)-$ | H | $CH_3$ | $CH_3$ | $CH_3$ | $CH_3$ | greenish-tinged yellow |
| 18b | H | H | $C_2H_5$ | $C_2H_5$ | $C_2H_5$ | $C_2H_5$ | greenish-tinged yellow |
| 19b | $CH_3-C(O)-NH-$ | H | $CH_3$ | $CH_3$ | $CH_3$ | $-CH(CH_3)_2$ | greenish-tinged yellow |
| 20b | $(CH_3)_2CH-$ | H | $CH_3$ | $CH_3$ | $CH_3$ | $-CH_2-C_6H_4-OCH_3$ | greenish-tinged yellow |
| 21b | $CH_3-C(CH_3)_2-CH_2-C(CH_3)_2-$ | H | $CH_3$ | $CH_3$ | $CH_3$ | $C_2H_5$ | greenish-tinged yellow |
| 22b | $C_2H_5O-$ | H | $CH_3$ | $CH_3$ | $CH_3$ | $CH_2-CH_2-Br$ | greenish-tinged yellow |
| 23b | $CH_3-SO_2-NH-$ | H | $CH_3$ | $CH_3$ | $CH_3$ | $C_2H_5$ | greenish-tinged yellow |
| 24b | $CH_3-CH_2-CH_2-C(O)-NH-$ | H | $CH_3$ | $CH_3$ | $CH_3$ | $CH_3$ | greenish-tinged yellow |
| 25b | $CH_3$ | H | $CH_3$ | $CH_3$ | $-CH_2-CH_2-CH_3$ | $C_2H_5$ | greenish-tinged yellow |

Table 1-continued

| No. | U¹ | U² | U³ | U⁴ | U⁵ | U⁶ | Colour shade on polyamide |
|---|---|---|---|---|---|---|---|
| 26b | $CH_3$ | | H | $CH_3$ | $CH_3$ | $-CH_2-CH_2-CH_2-CH_3$ | $C_2H_5$ | greenish-tinged yellow |
| 27b | $CH_3$ | | H | $CH_3$ | $C_3$ | $-CH_2-CH_2-CN$ | $C_2H_5$ | greenish-tinged yellow |
| 28b | $CH_3$ | | H | $CH_3$ | $CH_3$ | $-CH_2-\overset{O}{\underset{\|}{C}}-OCH_3$ | $C_2H_5$ | greenish-tinged yellow |
| 29b | $CH_3$ | | H | $CH_3$ | $CH_3$ | $-CH_2-CH_2-\overset{O}{\underset{\|}{C}}-OC_2H_5$ | $C_2H_5$ | greenish-tinged yellow |
| 30b | $CH_3$ | | H | $CH_3$ | $CH_3$ | $-CH_2-CH_2-Cl$ | $C_2H_5$ | greenish-tinged yellow |
| 31b | $CH_3$ | | H | $CH_3$ | $CH_3$ | $-CH_2-CH=CH_2$ | $C_2H_5$ | greenish-tinged yellow |
| 32b | $CH_3$ | | H | $CH_3$ | $CH_3$ | $-CH_2-C_6H_5$ | $C_2H_5$ | greenish-tinged yellow |

Table 2

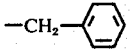

| No. | U | U³ | U⁴ | U⁵ | U⁶ | Colour shade on polyamide |
|---|---|---|---|---|---|---|
| 33b | 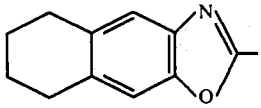 | $CH_3$ | $CH_3$ | $CH_3$ | $C_2H_5$ | greenish-tinged yellow |
| 34b | 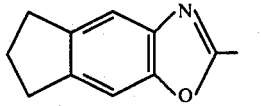 | $CH_3$ | $CH_3$ | $C_2H_5$ | $CH_3$ | greenish-tinged yellow |
| 35b | 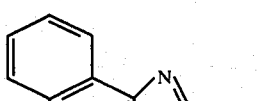 | $CH_3$ | $CH_3$ | $CH_3$ | $C_2H_5$ | yellow |
| 36b | 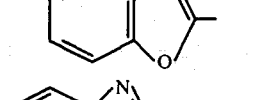 | $CH_3$ | $CH_3$ | $CH_3$ | $C_2H_5$ | greenish-tinged yellow |
| 37b | 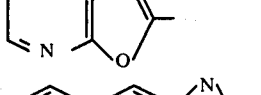 | $CH_3$ | $CH_3$ | $CH_3$ | $C_2H_5$ | yellow |
| 38b | 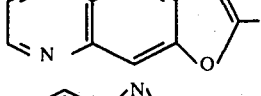 | $CH_3$ | $CH_3$ | $CH_3$ | $C_2H_5$ | greenish-tinged yellow |
| 39b | 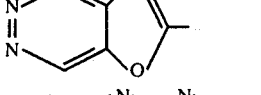 | $CH_3$ | $CH_3$ | $CH_3$ | $C_2H_5$ | yellow |
| 40b | 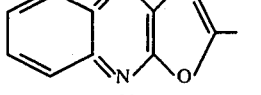 | $CH_3$ | $CH_3$ | $CH_3$ | $C_2H_5$ | greenish-tinged yellow |

Table 2-continued

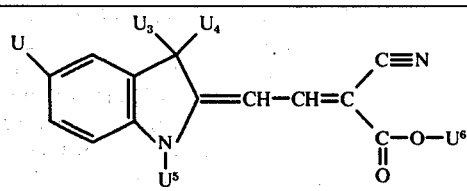

| No. | U | U³ | U⁴ | U⁵ | U⁶ | Colour shade on polyamide |
|---|---|---|---|---|---|---|
| 41b | (acenaphtho-oxazole) | $CH_3$ | $CH_3$ | $CH_3$ | $C_2H_5$ | yellow |
| 42b | (benzoxazole) | —$CH_2$—$(CH_2)_3$—$CH_2$— | | $CH_3$ | $C_2H_5$ | greenish-tinged yellow |
| 43b | (N-methyl benzimidazole) | $CH_3$ | $CH_3$ | $CH_3$ | $C_2H_5$ | greenish-tinged yellow |
| 44b | $CH_3$- (N-cyanoethyl methylbenzimidazole) | $CH_3$ | $CH_3$ | $CH_3$ | $C_2H_5$ | greenish-tinged yellow |
| 45b | $C_2H_5O$- (N-ethyl benzimidazole) | $CH_3$ | $CH_3$ | $CH_3$ | $C_2H_5$ | yellow |
| 46b | $CH_3$- (benzothiazole) | $CH_3$ | $CH_3$ | $CH_3$ | $C_2H_5$ | yellow |
| 47b | $CH_3O$- (benzothiazole) | $CH_3$ | $CH_3$ | $CH_3$ | $C_2H_5$ | yellow |
| 48b | Cl- (benzothiazole) | $CH_3$ | $CH_3$ | $CH_3$ | $C_2H_5$ | yellow |

EXAMPLE 2b

An approximately 0.1% strength dyeing with dyestuff 1b on polyamide-6 fabrics is produced as follows:

The fabric is introduced at 40°, using a liquor ratio of 1 : 40 to 1 : 30, into a dyebath which contains the finely divided dyestuff and 1 g per liter of a conventional anionic dispersing agent. The liquor temperature is raised to 98° (boiling point) over the course of 40 to 60 minutes, and is left at this temperature for about a further 60 minutes. Thereafter, the fabric is rinsed and dried. Strong greenish-tinged yellow dyeings of high clarity and excellent fastness properties are obtained.

Dyeings with similar valuable properties are obtained if instead of the dyestuff of the formula 1b one of the dyestuffs listed in Tables 1 and 2 of Example 1b are employed.

EXAMPLE 3b

An approximately 0.2% strength dyeing with dyestuff 2b on polyethylene terephthalate fabric is produced as follows:

The fabric is introduced at 50°, using a liquor ratio of 1 : 40, into a dyebath which contains the finely divided dyestuff, 1 g/l of a conventional anionic dispersing agent, 5 g/l of o- cresotonic acid methyl ester and 1 g/l of NaH$_2$PO$_4$, and is adjusted to pH 4.5–5 with acetic acid. The temperature is raised to 80°–85° over the course of 20 minutes and the bath is left in this temperature range for a further 20 minutes. Thereafter the liquor is gradually brought to the boil. After a period of boiling of about 1 hour, the dyeing process is complete. After rinsing and drying, greenish-tinged yellow dyeings of high clarity and very good fastness properties are obtained.

EXAMPLE 4b

An approximately 0.22% strength dyeing with dyestufff on cellulose triacetate fabric is produced in accordance with the method of dyeing indicated in Example 3b. The resulting strongly greenish-tinged dyeing displays high clarity and good fastness properties

EXAMPLE 5b

A knitted fabric of polyhexamethylenediamine adipate filaments is impregnated at room temperature with a solution which contains 6 parts of the dyestuff of the formula 10b (Example 1b, Table 1) and 7 parts of nonylphenol-heptaglycolether in 989 parts of tetrachloroethylene. After squeezing out to a weight increase of 60%, the knitted fabric is dried for 1 minute at 80°. Thereafter the dyestuff is fixed by heating the knitted fabric to 192° for 45 seconds. Small amounts of dyestuff which have not been fixed are then eluted by brief rinsing in cold tetrachloroethylene. After drying, a very clear, greenish-tinged yellow dyeing is obtained, which is distinguished by its high dyestuff yield, very good build-up and excellent fastness properties.

I claim:

1. Azolindoline of the formula

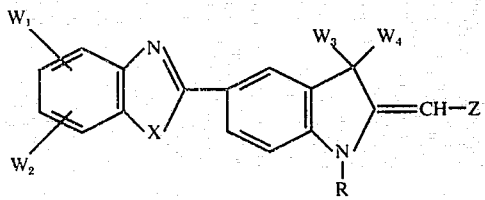

wherein
W$_1$ is hydrogen, alkyl of 1–5 carbon atoms, cyclohexyl, phenyl, chloro, alkoxy of 1–5 carbon atoms, methylsulfonyl, ethylsulfonyl, dimethylaminosulfonyl, diethylaminosulfonyl, dimethylaminocarbonyl, diethylaminocarbonyl, methoxycarbonyl, ethoxycarbonyl, methoxyethoxycarbonyl, acetylamino, propionylamino, methylsulfonylamino, or trifluoromethyl;
W$_2$ is hydrogen or alkyl of 1–5 carbon atoms;
W$_1$ and W$_2$ additionally can be joined together to produce a fused benzene ring;
W$_3$ and W$_4$ separately are methyl or ethyl, or can be joined together to produce a cyclopentyl or a cyclohexyl ring; Ser. No. 434,022
R is alkyl of 1–5 carbon atoms, chloroethyl, bromoethyl, fluoroethyl, cyanoethyl, allyl, methoxycabonylethyl, benzyl, or phenylethyl;
X is oxygen, sulfur, or =NR$_4$;
R$_4$ is hydrogen, alkyl of 1–5 carbon atoms, chloroethyl, bromoethyl, fluoroethyl, cyanoethyl, allyl, methoxycarbonylethyl, benzyl, phenylethyl, or cyclohexyl; and
Z represents —H, —CHO,

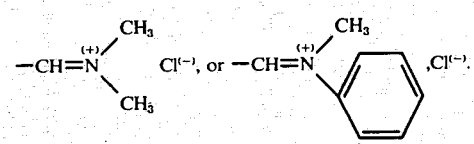

2. Azolindoline of clam 1 wherein Z is —CHO
3. Azolindoline of claim 1 wherein Z is hydrogen.
4. The compound of the formula

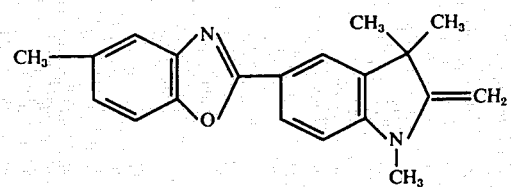

5. The compound of the formula

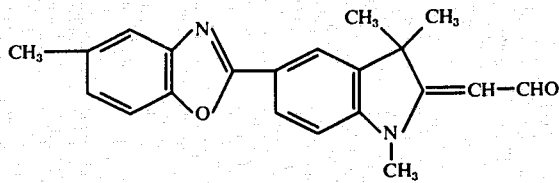

6. The compound of the formula

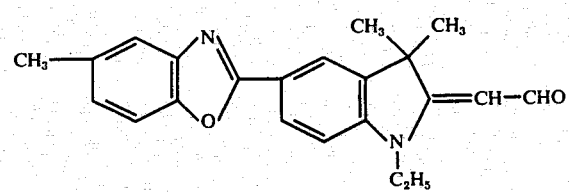

* * * * *